United States Patent [19]

Skinner

[11] Patent Number: 4,498,982
[45] Date of Patent: Feb. 12, 1985

[54] REVERSE OSMOSIS WATER PURIFICATION SYSTEM

[75] Inventor: Christopher A. Skinner, St. Petersburg, Fla.

[73] Assignee: Extracorporeal Medical Specialties, Inc., King of Prussia, Pa.

[21] Appl. No.: 439,680

[22] Filed: Nov. 8, 1982

[51] Int. Cl.³ .............................................. B01D 31/00
[52] U.S. Cl. ................................... 210/96.2; 210/186; 210/416.1; 210/433.2
[58] Field of Search .................. 210/652, 259, 96.1, 210/96.2, 186, 184, 433.2, 321.1, 416.1

[56] References Cited

U.S. PATENT DOCUMENTS

| | | | |
|---|---|---|---|
| 3,459,304 | 8/1969 | Brenchley | 210/96.2 X |
| 3,774,763 | 11/1973 | Yall et al. | 210/259 X |
| 3,899,421 | 8/1975 | Keilin et al. | 210/96.1 |
| 4,321,137 | 3/1982 | Kohler | 210/416.1 X |
| 4,344,826 | 8/1982 | Smith | 210/652 X |

*Primary Examiner*—Frank Spear
*Attorney, Agent, or Firm*—Mark A. Hofer

[57] ABSTRACT

A reverse osmosis system including a high pressure pump and pump motor is enclosed in an unvented enclosure to reduce the amount of noise which would otherwise be transmitted into the surrounding environment. The pump motor is cooled by the flow of inlet water through heat-conducting tubing arranged as by wrapping to be in thermal contact with the pump motor. The absorption of thermal energy by the inlet water provides an additional benefit in that product water flow during reverse osmosis is a function of temperature, with the higher temperature water yielding an increased product water flow. In a preferred embodiment of the present invention, the tubing coil is secured to the pump motor housing by a clamshell-like clamping assembly. The purity of the product water is monitored by a conductivity cell including first and second electrodes arranged to detect the conductivity of the water. At least one of the electrodes exhibits a screw-like shape, including a threaded body and a head which comprises the electrode in the flow of water. The central axis of the head which is parallel to the longitudinal axis of the threaded body is offset from the axis of the threaded body. A slot is located in the end of the body remote from the head which permits the electrode to be turned mechanically. Rotation of the body will thereby rotate the offset electrode head toward or away from the second electrode, thus permitting adjustment of the output of the conductivity cell without entering the water flow.

7 Claims, 5 Drawing Figures

REVERSE OSMOSIS WATER PURIFICATION SYSTEM

This invention relates to water purification systems and, in particular, to reverse osmosis and ultrafiltration fluid separation systems.

The need for purified water frequently arises in a medical setting. For instance, purified water is generally required when performing hemodialysis on a patient requiring such treatment. In hemodialysis, impurities in a patient's blood are removed by diffusing them across a membrane and into a specially prepared dialysate fluid. A considerable amount of dialysate fluid is required for a typical hemodialysis treatment, which fluid is generally prepared using purified water.

One technique used to purify water is the reverse osmosis process. In this process, a stream of untreated water is pumped at elevated pressure into a pressure resistant vessel containing a semipermeable membrane. Some of the water permeates across the membrane and is collected as purified product water in a low pressure output line while the remainder of the original stream exits the vessel, where it is depressurized for recirculation or disposal.

The amount of product water produced by reverse osmosis is a function of the elevated pressure of the untreated water in the membrane vessel. Considerable pressure is required to produce sufficient product water flux across a membrane of reasonable surface area. Generally, a linear relationship exists between product water flow and pressure. In order to attain the pressures of several hundred psi which are desirable for significant product water flows, a pump and pump motor of substantial capacity are required. Such a pump motor will produce a significant amount of heat, which must be dissipated to protect the motor. A conventional way to disperse the heat from the pump motor is to house the reverse osmosis system in a vented cabinet, and to use a fan to pull air through and out of the cabinet. In a clinical or hospital setting, however, venting of the system is undesirable, because of the noise of the fan and pump motor. It is preferable in such a setting for the system to be enclosed in an unvented enclosure so that some degree of soundproofing is afforded.

In accordance with the principles of the present invention, a reverse osmosis system including a high pressure pump and pump motor is enclosed in an unvented enclosure to reduce the amount of noise which would otherwise be transmitted into the surrounding environment. The pump motor is cooled by the flow of inlet water through heat-conducting metallic tubing arranged as by wrapping to be in thermal contact with the pump motor. The absorption of thermal energy by the inlet water provides an additional benefit in that product water flow during reverse osmosis is a function of temperature, with the higher temperature water yielding an increased product water flow.

In an illustrated embodiment of the present invention, the inlet water tubing comprises copper tubing which is coiled around the pump motor housing and bonded thereto by thermally conductive epoxy or adhesive sealant. In a preferred embodiment of the present invention, the tubing coil is secured to the pump motor housing by a clamshell-like clamping assembly.

The degree of purity of the product water may be monitored by sensors which detect impurities by sensing ion concentrations in the inlet and product water streams. The ion concentrations may be detected by conductively cells, which produce signal which can be compared to determine system operational efficiency.

In accordance with the principles of a further aspect of the present invention, a conductivity cell is provided including first and second electrodes arranged to detect the conductivity of water in a reverse osmosis system. At least one of the electrodes exhibits a screw-like shape, including a threaded body and a head which comprises the electrode in the flow of water. The central axis of the head which is parallel to the longitudinal axis of the threaded body is offset from the axis of the threaded body. A slot is located in the end of the body remote from the head which permits the electrode to be turned mechanically. Rotation of the body will thereby rotate the offset electrode head toward or away from the second electrode, thus permitting adjustment of the output of the conductivity cell without entering the water flow.

Figure 1:
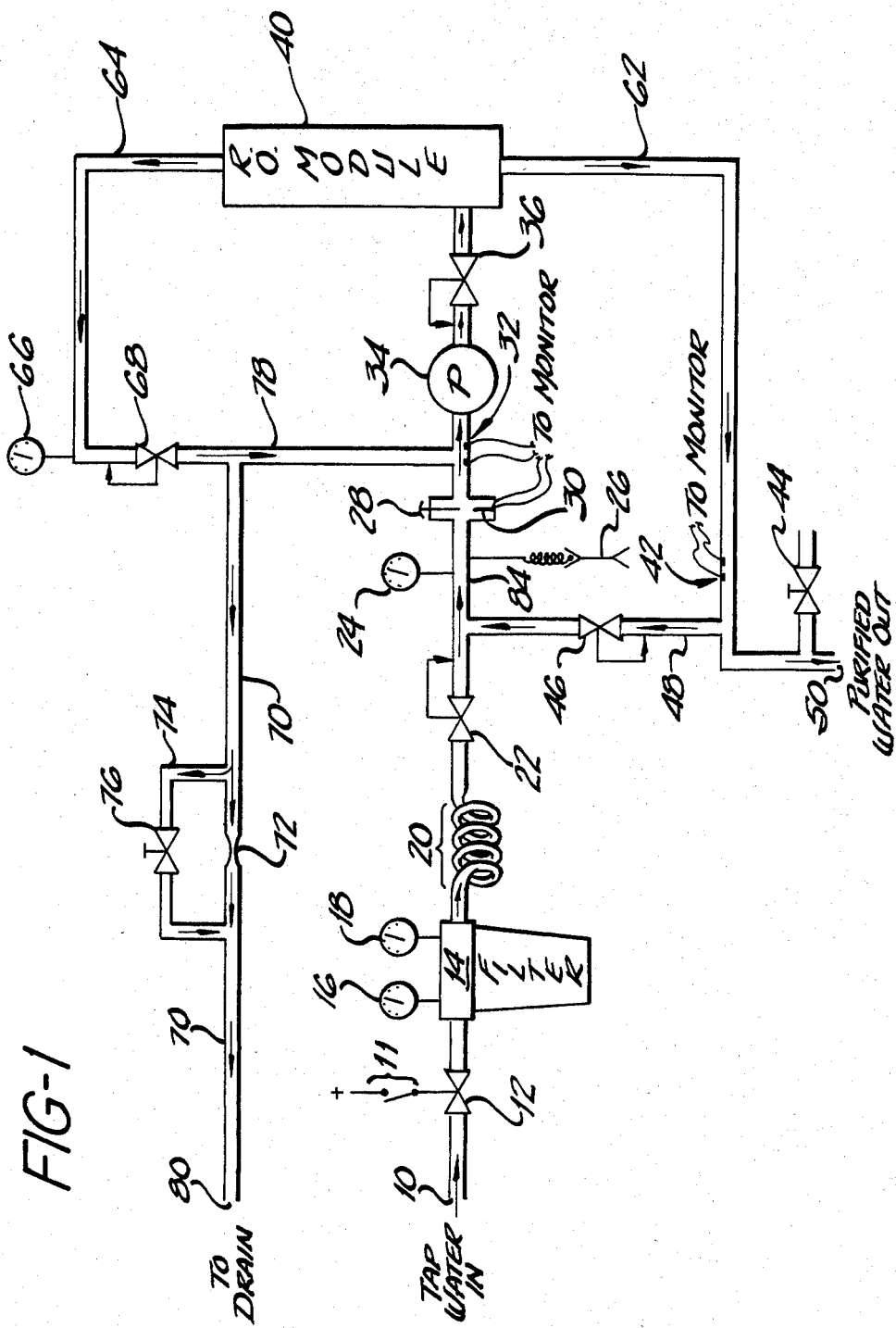
FIG. 1 illustrates schematically a reverse osmosis water purification system constructed in accordance with the principles of the present invention.

Referring to FIG. 1, a reverse osmosis system constructed in accordance with the principles of the present invention is shown schematically. Untreated tap water enters the system through an inlet 10, and is passed by an inlet solenoid valve 12 under control of an on/off switch 11. The inlet water enters a filter 14, which filters out particulate matter and removes the chlorine from the inlet water. The filter includes a ten micron carbon impregnated filter element. The chlorine must be removed since chlorine can damage the membrane used in the reverse osmosis module. The water pressure at the inlet and outlet of the filter 14 is monitored by gauges 16 and 18. During normal operation the gauge pressure should be virtually the same. A greater than 10 psi differential between the inlet and outlet gauges of the filter 14 indicates that the filter is becoming clogged and should be replaced.

The filtered water then flows through a coil of tubing 20, which is wound around the motor and will be described in further detail in conjunction with FIG. 2. The inlet water then flows through a pressure regulator 22. The pressure regulator 22 controls the water pressure at its outlet so that the water pressure will not exceed 20 psi. Depending upon the pressure of the inlet water, water pressure at the input to the pressure regulator can exceed 20 psi. A flow of inlet water, now at approximately 20 psi, enters the inlet line 84 to the pump and reverse osmosis module.

In the inlet line 84, a pressure gauge 24 monitors water pressure to insure that water pressure remains at about 20 psi. A one psi check valve 26 is coupled to the inlet line 84 to inject formalin into the inlet water. The injected formalin is used to sanitize the water since the water now has no chlorine content. The inlet water flows past a pressure switch 28, which turns the system off if water pressure in the inlet line 84 drops below 6 psi. The pressure switch 28 thereby protects the pump against cavitation. A temperature sensor 30 senses the inlet water temperature and provides an output signal to a monitor (not shown). The inlet water also flows past a conductivity cell 32, which also provides an electrical signal for the monitor.

The inlet water then enters the pump 34, which increases the water pressure from about to 20 psi to approximately 200 psi. The pressurized water is applied to the reverse osmosis module 40 by way of a 25 psi check valve 36. This check valve 36 closes when the outlet water pressure of the pump drops below 25 psi to prevent the instantaneous reflection of high water pressure back to the gauge 24 when the pump 34 is turned off. This is to protect the gauge and other components in the low pressure 20 psi loop preceding the pump.

Inlet water, now at 200 psi enters the reverse osmosis module 40 where some of the water permeates the module membrane to produce purified product water in outlet line 62. The balance of the inlet water which does not permeate the membrane exits the module through a line 64. The module outlet pressure in line 64 remains at about 200 psi and is monitored by a pressure gauge 66. The reverse osmosis membrane may comprise, for example, a thin-film composite membrane formed by a depositing a thin polymer coating on a microporous polysulfone support layer.

The water pressure in the outlet line 64 is maintained at approximately 200 psi by a back pressure regulator 68, which opens when the water pressure in line 64 exceeds 200 psi. Water passed by the back pressure regulator flows into a drain line 70 and a recirculation line 78. The water in the recirculation line 78 reenters the inlet line 84 at a point opposite the conductivity cell 32. Water in the drain line 70 passes through a 500 cc per minute orifice 72 and then to the drain through an outlet 80. A line 74 bypasses the orifice 72 during rinsing operations, at which time the rinse valve 76 is opened.

Purified product water in line 62 flows past a conductivity cell 42, which detects the level of impurities remaining in the water. The purified water then is free to flow out of an outlet 50. A sampling port 44 may be opened if it is desirable to take a sample of the purified water. When the both the sampling port 44 and the outlet 50 are closed, the purified water pressure builds in a return line 48, which soon opens a one psi check valve 46. The unused purified water then recirculates through the system by reentering the inlet line 84.

Figure 2:
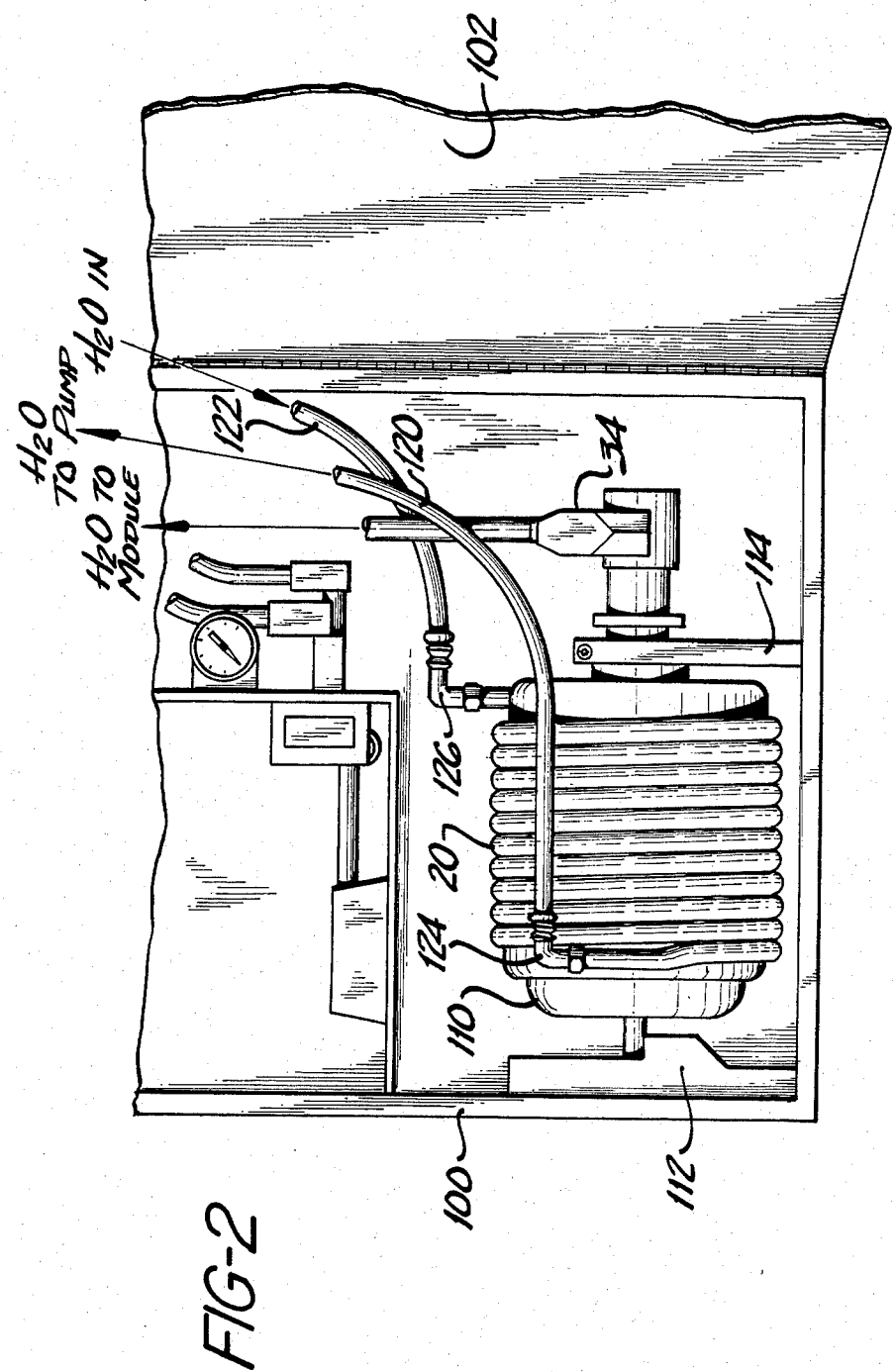
FIG. 2 is a frontal view of a pump motor and cooling coil of a reverse osmosis system arranged in accordance with the principles of the present invention.

The arrangement of FIG. 1 is assembled in a cabinet 100 as shown in FIG. 2. The system is fully enclosed when cabinet door 102 is closed. The pump 34 is driven by a pump motor 110, which may be a one-third horsepower motor. The pump motor 110 is suspended between motor mounts 112 and 114. Inlet water flows through polypropylene tubing 122, which is connected to copper tubing coil 20 by an elbow compression fitting 126. The tubing coil 20 is comprised of approximately 40 feet of one-quarter inch or three-eighth inch diameter copper tubing wound around the motor 110 and held in place by thermally conductive epoxy or a thermally conductive silicone rubber adhesive sealant. The outlet end of the copper tubing is connected by an elbow compression fitting 124 to an outlet line of polypropylene tubing 120.

The input water in the tubing section 122 exhibits a temperature between 40° F. and 85° F. As the input water flows through the copper tubing, it cools the motor by absorbing heat from the motor housing with which it is in contact. The inlet water returning through tubing section 120 typically exhibits a temperature increase of 3° to 4° F. as compared with the inlet water in tubing section 122. The output rate of purified water from the reverse osmosis module depends upon the temperature of the input water, and varies from approximately 500 milliliters per minute at 40° F. to approximately 1000 milliliters per minute at 85° F. The relationship between water output rate and temperature is typically a linear one, and it has been found that the product water rate can be increased by 75 to 100 milliliters per minute by virtue of the heating provided by the pump motor.

Figure 3:
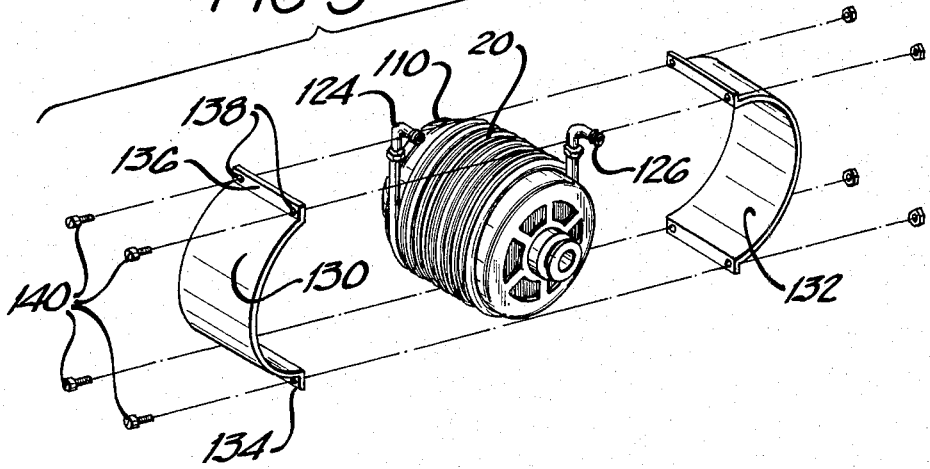
FIG. 3 illustrates a clamshell-like arrangement for clamping a cooling coil to a pump motor.

A preferred arrangement for securing the copper tubing coil 20 to the pump motor 110 is shown in FIG. 3. Two pieces of sheet metal 130 and 132 are each formed in almost a semicircle with a curvature approximately matching half the outer circumference of the coil of tubing 20. The ends of the curve pieces of metal 134 and 136 are folded back to form flanges. Holes shown at 138 are drilled in the two flanges. The copper tubing is wound around the motor and the curved pieces of metal 130 and 132 are placed on the front and rear of the copper tubing coil. The two pieces of curve metal are then bolted together in a clamshell-like arrangement by bolts 140. Use of the assembly shown in FIG. 3 to hold the tubing coil in place has been found to be faster to assemble and to require less labor than the use of epoxy or sealant.

Figure 4:
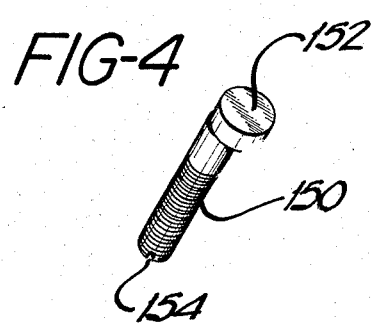
FIG. 4 illustrates an electrode for a conductivity cell of a reverse osmosis system constructed in accordance with the principles of the present invention.

The conductivity cells 32 and 42 of the reverse osmosis systems of FIG. 1 each include metal pin electrodes as shown in FIG. 4. Each electrode resembles a screw with a threaded body 150 and a cylindrical head 152. The longitudinal axis of the threaded body 150 is offset from the central axis of the cylindrical head 152. A slot 154 is located in the end of the body 150 remote from the head 152.

Figure 5:
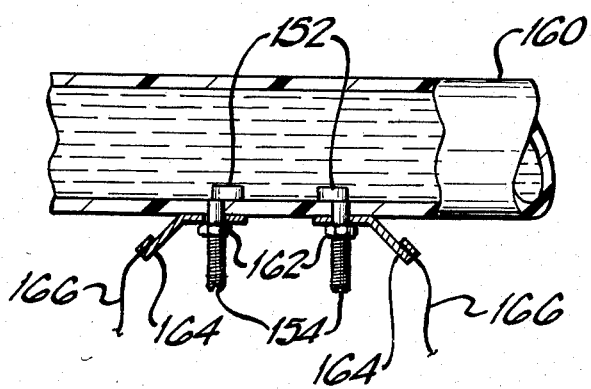
FIG. 5 illustrates electrodes as shown in FIG. 4 in a reverse osmosis system conductivity cell.

Electrodes as shown in FIG. 4 are arranged to form a conductivity cell as shown in FIG. 5. A section of PVC tubing 160, through which water to be monitored flows, is drilled with two holes spaced apart a nominal distance for the electrodes. The electrodes are screwed into the holes with the heads 152 being located in the water path. Solder lugs 164 connected to wires 166 are slipped over the threaded electrode at the outside of the tube 160 and are secured in place with nuts 162.

During assembly, the electrode heads are adjusted to be spaced apart by a distance which gives a known output signal for water of a known conductivity. When water of a known conductivity is flowing through the tubing segment 160 and the conductivity cell is energized, a screwdriver may be inserted in slot 154 to turn the electrodes so that their heads move toward and away from each other until the desired output signal is produced. Set-up of the conductivity cell is thus simple and does not require intrusion into the water path.

What is claimed is:

1. In a reverse osmosis water purfication system, a conductivity cell for sensing the conductivity of water, including first and second electrodes which are in contact with said water, at least one of said electrodes comprising:

a generally cyclindrical threaded body having a central longitudinal axis;

an electrode head located at one end of said threaded body and having a central axis which is substantially parallel to said central longitudinal axis and is offset therefrom; and a slot located in the end of said threaded body remote from said electrode head end.

2. The arrangement of claim 1, wherein said water purification system includes a pipe into which purified water flows, said electrodes extending through a wall of said pipe with said electrode head of at least one of said electrodes being located in the interior of said pipe in contact with said purified water with said slot end of said at least one of said electrodes being located outside of said pipe.

3. The arrangement of claim 1, further comprising means for connecting wires to said electrodes outside said pipe.

4. In a reverse osmosis water purification system, including a module containing a semipermeable membrane and having an inlet port for receiving water to be purified and an outlet port at which purified product water is produced; means for supplying water to be purified to said inlet port comprising:

a pump having an inlet, and an outlet connected to said module inlet port;

a pump motor connected to said pump for activating said pump;

a thermally conductive tubing segment having an inlet for receiving water to be purified and an outlet connected to said inlet of said pump, said tubing segment being thermally connected to said pump motor so as to enable a transfer of thermal energy from said pump motor to said water to be purified, wherein said thermally conductive tubing segment comprises a coil of metallic tubing wrapped around said pump motor;

first and second substantially curved sheets of metal, each having a flange at each end of the curved portion thereof, said curved sheets being located on opposing sides of said pump motor and wrapped tubing assembly so as to enclose said assembly, wherein opposing flanges of said curved sheets of metal are connected to each other so as to fixedly retain said coil of metallic tubing in thermal contact with said pump motor.

5. In a reverse osmosis water purification system, including a module containing a semipermeable membrane and having an inlet port for receiving water to be purified and an outlet port at which purified product water is produced; means for supplying water to be purified to said inlet port comprising:

a pump having an inlet, and an outlet connected to said module inlet port;

a pump motor connected to said pump for activating said pump;

a thermally conductive tubing segment having an inlet for receiving water to be purified and an outlet connected to said inlet of said pump, said tubing segment being thermally connected to said pump motor so as to enable a transfer of thermal energy from said pump motor to said water to be purified, said thermally conductive tubing segment comprising a coil of metallic tubing wrapped around said pump motor; and wherein said module further includes a second outlet port at which unpurified pressurized water is produced, and further comprising: a first water path, connected between said second outlet port of said module and said inlet of said pump to return at least a portion of said unpurified pressurized water to said inlet of said pump, said first water path including means for reducing the pressure of said returned water; and a second water path, connected between said outlet port at which purified product water is produced and said inlet of said pump, for selectively recirculating purified product water through said module.

6. The arrangement of claim 5, further comprising:

a first conductivity cell located in said pump inlet; and a second conductivity cell located in said second water path.

7. The arrangement of claim 5, further comprising:

a carbon filter having an inlet for receiving water to be purified and an outlet connected to said inlet of said coil of copper tubing.

* * * * *